(12) United States Patent
Tanguay et al.

(10) Patent No.: US 11,994,465 B2
(45) Date of Patent: May 28, 2024

(54) SYSTEMS AND METHODS FOR MEASURING TRACE CONTAMINANTS IN GAS MATRIX USING INTEGRATED CAVITY OUTPUT SPECTROSCOPY

(71) Applicant: ABB Schweiz AG, Baden (CH)

(72) Inventors: François Tanguay, Lévis (CA); Kyle Owen, Lompoc, CA (US); John Brian Leen, Sunnyvale, CA (US); Axel Meunier, Québec (CA); Bertrand Simon Lanher, San Jose, CA (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 17/849,395

(22) Filed: Jun. 24, 2022

(65) Prior Publication Data

US 2023/0417663 A1   Dec. 28, 2023

(51) Int. Cl.
*G01N 21/39* (2006.01)
*G01N 21/03* (2006.01)

(52) U.S. Cl.
CPC .......... *G01N 21/39* (2013.01); *G01N 21/031* (2013.01); *G01N 2021/399* (2013.01); *G01N 2201/0612* (2013.01); *G01N 2201/0636* (2013.01)

(58) Field of Classification Search
CPC ............. G01N 21/39; G01N 21/031; G01N 2021/399; G01N 2201/0612; G01N 2201/0636
USPC ...................................................... 356/437
See application file for complete search history.

(56) References Cited

U.S. PATENT DOCUMENTS

| | | | |
|---|---|---|---|
| 10,495,570 B2 | 12/2019 | Owen | |
| 2002/0176255 A1* | 11/2002 | Yamauchi | H04N 9/3167 362/346 |
| 2002/0186741 A1* | 12/2002 | Kleinschmidt | B23K 26/705 372/57 |
| 2003/0161357 A1* | 8/2003 | Bolshtyansky | H01S 3/094003 372/6 |
| 2004/0105468 A1* | 6/2004 | Killinger | H04B 10/1121 372/20 |
| 2004/0182143 A1* | 9/2004 | Black | F01D 17/08 73/112.01 |

(Continued)

FOREIGN PATENT DOCUMENTS

| | | | | |
|---|---|---|---|---|
| CN | 109085133 A | | 12/2018 | |
| CN | 112255815 A | * | 1/2021 | ............. G02B 27/30 |

OTHER PUBLICATIONS

Feng Dong et al., "Rapid, Online Quantification of H2S in JP-8 Fuel Reformate Using Near-Infrared Cavity-Enhanced Laser Absorption Spectroscopy", Analytical Chemistry 83, pp. 4132-4136 (2011).

(Continued)

*Primary Examiner* — Md M Rahman
(74) *Attorney, Agent, or Firm* — Armstrong Teasdale LLP

(57) ABSTRACT

A laser absorption spectrometry system for gas measurement is provided. The system includes an integrated cavity output spectroscopy (ICOS) assembly. The assembly includes a gas cell including a cell body defining an optical cavity, one or more tunable diode lasers having one or more nominal wavelengths, and a reflective collimation mirror positioned in an optical path between the one or more tunable diode lasers and the gas cell.

20 Claims, 22 Drawing Sheets
(9 of 22 Drawing Sheet(s) Filed in Color)

(56) References Cited

U.S. PATENT DOCUMENTS

| | | | |
|---|---|---|---|
| 2007/0076209 A1* | 4/2007 | Baer | G01N 21/39 |
| | | | 356/519 |
| 2008/0092648 A1* | 4/2008 | Zhou | G01N 21/3554 |
| | | | 73/335.01 |
| 2008/0123712 A1* | 5/2008 | Zhou | G01N 21/39 |
| | | | 372/55 |
| 2009/0059234 A1* | 3/2009 | Dreyer | G01J 3/02 |
| | | | 356/437 |
| 2013/0286397 A1 | 10/2013 | Witinski | |
| 2015/0355091 A1* | 12/2015 | Conroy | G01N 33/2882 |
| | | | 250/459.1 |
| 2017/0248517 A1* | 8/2017 | Scherer | G01N 21/0332 |
| 2018/0095031 A1 | 4/2018 | Owen | |
| 2019/0128799 A1 | 5/2019 | Leen | |

OTHER PUBLICATIONS

European Search Report for European Application No. 23181000.3, published Dec. 4, 2023, 9 pps.
European Search Report for European Application No. 23180982.3, published Nov. 24, 2023, 9 pps.
Centeno R. et al: "Sensitivity enhancement in off-axis integrated cavityoutput spectroscopy",Optics Express, vol. 22, No. 23, Nov. 4, 2014 (Nov. 4, 2014), p. 27985.

* cited by examiner

Most Significant Etalons Correspond to the Following Cavities L-Values:

| Seconds | meters | Assignment | Amplitude Norm Mean | Amplitude Norm Var | R^2 Ampl.T°C | |
|---|---|---|---|---|---|---|
| 3.909E-11 | 0.012 | Focus Lens-Detector | 0.245 | 1.000 | 0.1226 | |
| 1.173E-10 | 0.035 | Collimator-Input Mirror | 0.236 | 0.266 | 0.0028 | 402-3 |
| 3.128E-10 | 0.094 | ~1*L | 0.546 | 0.590 | 0.0080 | 402-1 |
| 2.111E-09 | 0.633 | ~4*L | 1.000 | 0.488 | 0.0091 | |
| 2.17E-09 | 0.650 | ~4*L | 0.818 | 0.462 | 0.1443 | 402-3 |
| 2.209E-09 | 0.662 | ~7*L | 0.828 | 0.409 | 0.0880 | |
| 2.268E-09 | 0.680 | ~7*L | 0.819 | 0.345 | 0.0372 | |

SYSTEMS AND METHODS FOR MEASURING TRACE CONTAMINANTS IN GAS MATRIX USING INTEGRATED CAVITY OUTPUT SPECTROSCOPY

BACKGROUND

The field of the disclosure relates generally to systems and methods of measuring gases, and more particularly, to systems and methods of measuring contaminants in gases using integrated cavity output spectroscopy (ICOS).

Whenever fuel gas such as natural gas, coal syngas, or biogas, is generated, transferred, or used, levels of contaminants are typically required for the process. Measurements of various contaminants, e.g., $H_2S$, $H_2O$, $O_2$, and $CO_2$, are critical in preventing infrastructure damage due to corrosion or chemical reactivity. Natural gas producers must clean extracted gas to remove contaminants and then verify residual levels before introducing natural gas into a pipeline. Desulfurizer beds in fuel reformers need periodic replacement or regeneration to prevent $H_2S$ breakthrough into the reformed fuel product, and therefore frequent contaminant level monitoring is needed.

ICOS is a powerful tool in measuring gases. Known system and methods are disadvantaged in some aspects and improvements are desired.

BRIEF DESCRIPTION

In one aspect, a laser absorption spectrometry system for gas measurement is provided. The system includes an integrated cavity output spectroscopy (ICOS) assembly. The assembly includes a gas cell including a cell body defining an optical cavity, one or more tunable diode lasers having one or more nominal wavelengths, and a reflective collimation mirror positioned in an optical path between the one or more tunable diode lasers and the gas cell.

In another aspect, a laser absorption spectrometry system for gas measurement is provided. The system includes an ICOS assembly. The assembly includes a gas cell including a cell body defining an optical cavity, three or more tunable diode lasers having three or more nominal wavelengths and configured to emit three or more laser light in three or more wavelength ranges, and a combiner configured to combine the three or more laser light into a combined laser light configured to be coupled into the optical cavity.

DRAWINGS

These and other features, aspects, and advantages of the present disclosure will become better understood when the following detailed description is read with reference to the accompanying drawings in which like characters represent like parts throughout the drawings.

The patent or application file contains at least one drawing executed in color. Copies of this patent or patent application publication with color drawing(s) will be provided by the Office upon request and payment of the necessary fee.

DETAILED DESCRIPTION

The disclosure includes systems and methods of measuring trace contaminants in gas matrix using integrated cavity output spectroscopy (ICOS). Method aspects will be in part apparent and in part explicitly discussed in the following description.

Measurement of various contaminants, e.g. $H_2S$, $H_2O$, $O_2$, and $CO_2$, in fuel gas is needed for preventing infrastructure damage and for compliance with operation requirements. Corrosion from $H_2S$, $CO_2$, $H_2O$ and $O_2$ cause leaks to downstream assets. $H_2S$ is deadly even at low parts per million (ppm) values. Excess $H_2O$ leads to hydrates that decrease flow capacity and potential blockage. Excess $O_2$ degrades gas processing chemicals such as amines. In addition, $H_2S$, $CO_2$, $H_2O$ and $O_2$ have no energy value, and therefore are desirable to be removed from fuel gases.

In known systems, separate analyzers are used to analyze amounts of trace contaminants for individual contaminants. Optical interferences from strong broadband absorbers such as $CH_4$ in the natural gas matrix typically limit the performance of spectroscopic measurements. Fast response is often enabled by flowing large amounts of gas through the analyzer and therefore exchanging gas quickly inside the analyzer. Often the gas is not returned to the process and instead is released into the environment, which is costly and pollutes the environment because $CH_4$ is a green-house gas. As a result, using multiple analyzers increases the cost and pollution.

In contrast, systems and methods described herein use one ICOS system to analyze multiple contaminants by injecting a plurality of lasers at a plurality of nominal wavelengths into a gas cell of the ICOS system, thereby reducing costs and pollution to the environment and reducing response time.

In systems and methods described herein, a collimation lens may be replaced with a reflective collimation mirror, which facilitates injection of lasers at different wavelengths and reduces optical interferences or etalons, thereby simplifying the system design and increasing the accuracy and precision of measurements of contaminants. The accuracy and precision may be further improved by adjusting parameters of the ICOS system, such as the radius of curvature of cavity mirrors of the ICOS system, the cavity length, the launch angle of the laser beam, the divergence angle of the laser beam, and the launch distance of the laser beam. The parameters may be adjusted jointly or separately. Further, a gradient index (GRIN) lens may be used in the collimator to reduce etalons.

Figure 1:
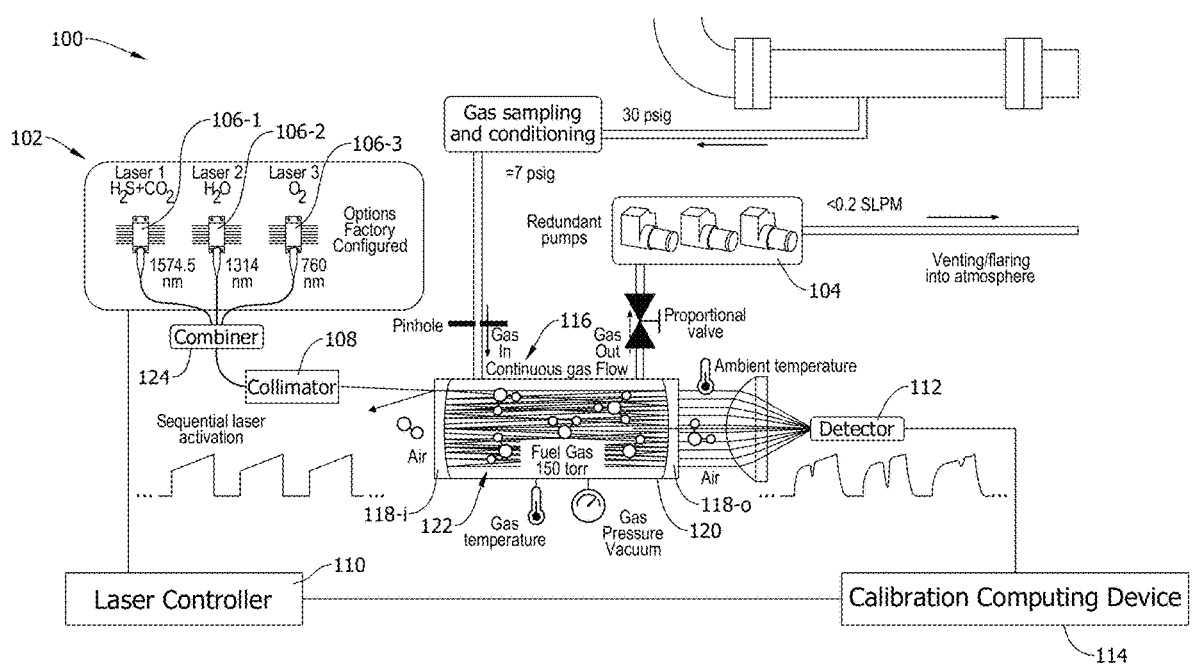
FIG. 1 is a schematic diagram of an integrated cavity output spectroscopy (ICOS) system.

FIG. 1 is a schematic diagram of an exemplary laser absorption spectrometry system 100. In the exemplary embodiment, system 100 includes an ICOS assembly 102 and a plurality of pumps 104. Pumps 104 are mounted in parallel such that one pump is running while other pumps are on standby. Running pump 104 is changed periodically to avoid overuse of any one pump 104. Periodic validation of the pump health and performance is conducted and allows predictive maintenance activities to be scheduled. A fault on pump 104 may be detected during the periodic validation and predictive maintenance may be performed before failure. A fault on pump 104 may also be detected immediately by a pressure sensor, reducing or eliminating downtime by switching to a back-up pump 104 instantaneously.

In the exemplary embodiment, ICOS assembly 102 includes one or more diode lasers 106, a gas cell 116, and a detector 112. Diode laser 106 may be a tunable near-infrared diode laser, where diode laser 106 may be tuned to emit laser light in a certain wavelength range. ICOS assembly 102 further includes a collimator 108 for focusing the laser light emitted by lasers 106. Collimator 108 may include a collimation lens. A collimation lens may be a spherical or aspherical lens. In some embodiments, collimator 108 includes a reflective collimation mirror 501 (see FIG. 5B described later). In other embodiments, collimator 108 includes a GRIN lens. Gas cell 116 includes a cell body 120 defining an optical cavity 122. Gas cell 116 further includes an input mirror 118-$i$ and an output mirror 118-$o$. Input and output mirrors 118 are positioned at two opposing ends of optical cavity 122. Input and output mirrors 118-$i$, 118-$o$ are highly reflective, having reflectance approximately 99.995%.

In the exemplary embodiment, system 100 may further include an ICOS computing device (not shown) and a laser controller 110. Laser controller 110 and the ICOS computing device may be part of ICOS assembly 102, or may be separate components from ICOS assembly 102. Laser controller 110 is configured to control diode laser 106 of ICOS assembly 102. Signals detected by detector 112 of ICOS assembly 102 are received and processed by the ICOS computing device. System 100 may include an ICOS calibration computing device 114 configured to calibrate and optimize parameters of system 100. ICOS calibration computing device 114 may be included in the ICOS computing device, or may be a separate computing device from the ICOS computing device. ICOS calibration computing device 114 may be in communication with detector 112, through wired or wireless communication. In some embodiments, ICOS calibration computing device 114 is a server computing device. In one example, ICOS calibration computing device 114 may receive data collected by detector 112 through a portable storage device, such as a flash drive or a thumb drive.

Figure 2A:
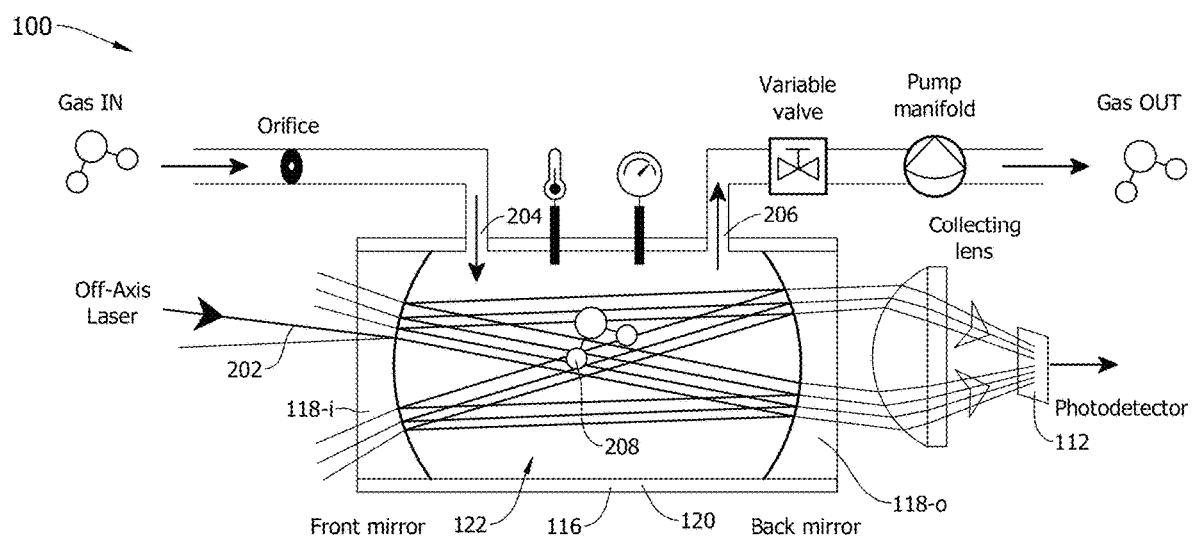
FIG. 2A is a schematic diagram showing the operation of the system shown in FIG. 1.
Figure 2B:
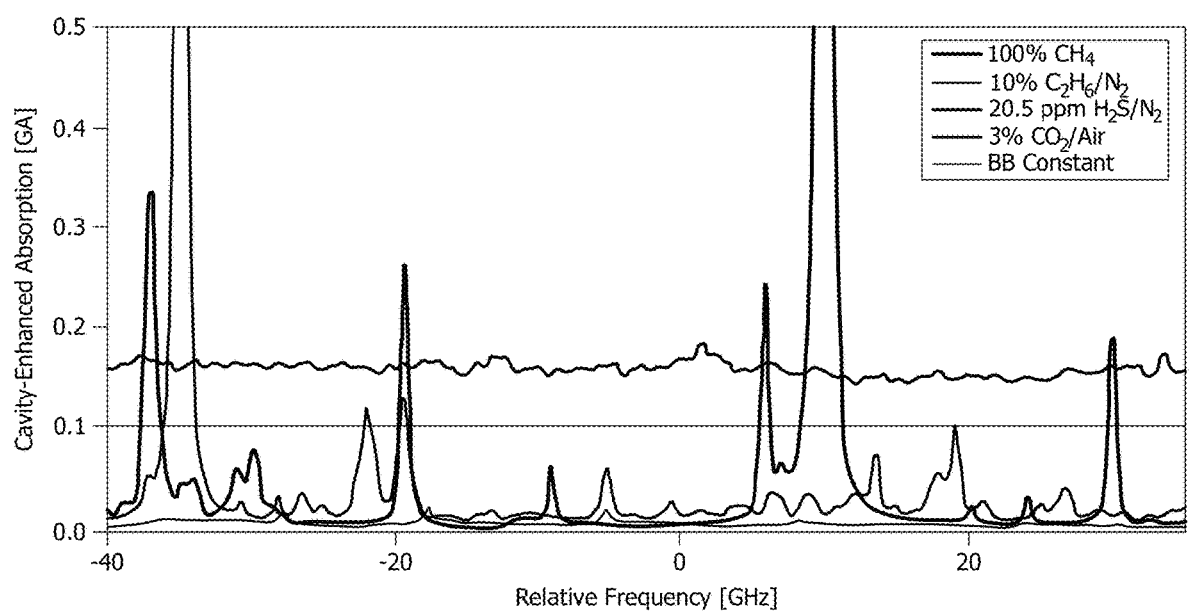
FIG. 2B shows representative absorption spectra of gases.

FIGS. 2A and 2B shows the operation mechanism of system 100. FIG. 2A is a schematic diagram showing the operation of system 100. FIG. 2B shows representative absorption spectra of gases. In operation, laser light 202 from diode lasers 106 (FIG. 1) is coupled off-axis or at a non-zero angle with z-axis or axis 602 of optical cavity 122 (see FIG. 6A described later) into gas cell 116 through input mirror 118-$i$ and exit from output mirror 118-$o$ while gas to be analyzed flows into optical cavity 122 through a gas inlet 204 and exit from optical cavity 122 from a gas outlet 206 of cell body 120. An ICOS assembly operated with light coupled off-axis into gas cell 116 may be referred to as an off-axis ICOS assembly. Light 202 is reflected back and forth within optical cavity 122, travelling a relatively long effective optical path length and therefore increasing the interaction path length between light 202 and gas 208. As a result, the optical absorption of gas is increased to a detectable level and is used to quantify gas concentrations, even for gases at low concentrations or weakly absorbing gas. Near-infrared detector 112 measures the light exiting from cell body 120 and the measurements from detector 112 are used to measure gases. As shown in FIG. 2B, different gases have different absorption spectra. The spectra are used to measure the content of gases in fuel gases.

Referring back to FIG. 1, system 100 is configured to measure multiple contaminants using one ICOS system, unlike in a known method, where separate analyzers are used to measure different contaminants, incurring additional costs and having increased negative environmental impact and fuel gas wastage.

In the exemplary embodiments, system 100 includes a plurality of lasers 106 having a plurality of nominal wavelengths. In one example, to measure contaminants $H_2S$, $CO_2$, $H_2O$, and $O_2$, three lasers 106-1, 106-2, 106-3 are used. Laser 106-1 has a nominal wavelength of 1574.5 nm. Laser 106-2 has a nominal wavelength of 1314 nm. Laser 106-3 has a nominal wavelength of 760 nm. During the operation of laser 106, a range of wavelengths below and/or above the nominal wavelength of laser 106 is scanned across. For example, if a laser 106 having a nominal wavelength of 1574.5 nm is used, a wavelength range of 1574.1 nm-1575.3 nm may be scanned across in operation, where the wavelength of output light by laser 106 may range from 1574.1 nm to 1575.3 nm. The selected nominal wavelengths correspond to absorption ranges of target gases. At the absorption ranges, the target gases are relatively absorbent and the absorption yields signals detectable by detector 112. For example, the nominal wavelength of 1574.5 nm corresponds to absorption ranges of $H_2S$ and $CO_2$. Because $H_2S$ and $CO_2$ have different absorption spectra, measurements of $H_2S$ and $CO_2$ may be obtained by using one laser at one nominal wavelength and separating the measurements using the different absorption spectra. The nominal wavelength of 1314 nm corresponds to the absorption range of $H_2O$. The nominal wavelength of 760 nm corresponds to the absorption range of 02. The laser light emitted by lasers 106-1, 106-2, 106-3 are combined in a combiner 124 into single laser light. The combined laser light may be sequential where laser light at different nominal wavelengths is emitted sequentially. Alternatively, laser light from lasers 106 is multiplex using dichroic mirrors or fiber combiners 124 that use wavelength division multiplexing. In some embodiments, combiner 124 is not used. The plurality of lasers are separately launched or injected into optical cavity 122. The number of lasers 106 that may be included in system 100 is limited by the size and mount of collimator 108. Therefore, a reduced-sized optical cavity 122, such as an optical cavity having 1 inch (2.54 cm) in diameter, may not have physical space for two or more launching devices for a plurality of lasers. In some embodiments, the positions of collimator 108 are offset from one another.

Referring back to FIG. 2A, combined laser light 202 is input into a collimator 108 and injected into gas cell 116. As a result, system 100 is used to measure concentrations of all trace contaminants with one single gas cell 116, reducing gas volume and methane leakage and resulting in shortened response time to allow for real-time monitoring of contaminants. Real-time monitoring of $H_2S$, $CO_2$, $H_2O$ and $O_2$ allows triggering of threshold alarms to redirect contaminated streams that would otherwise compromise safety and operational yield.

Besides being configured to measure two or more contaminants using one analyzer, instead of multiple analyzers, system 100 also provides flexibility over conventional systems. System 100 may be used to measure one, two, or more contaminants, and may be used to measure any combinations of contaminants. $H_2S$, $CO_2$, $H_2O$, and $O_2$ are described herein as examples only. System 100 may be used to measure other contaminants or any combination of $H_2S$, $CO_2$, $H_2O$, and $O_2$ in addition to other contaminants. Lasers having wavelengths corresponding to absorption ranges of other contaminants may be used or added to system 100. Alternatively, lasers may be tuned to the wavelength ranges corresponding to the absorption range of the contaminants to be measured.

Figure 3:
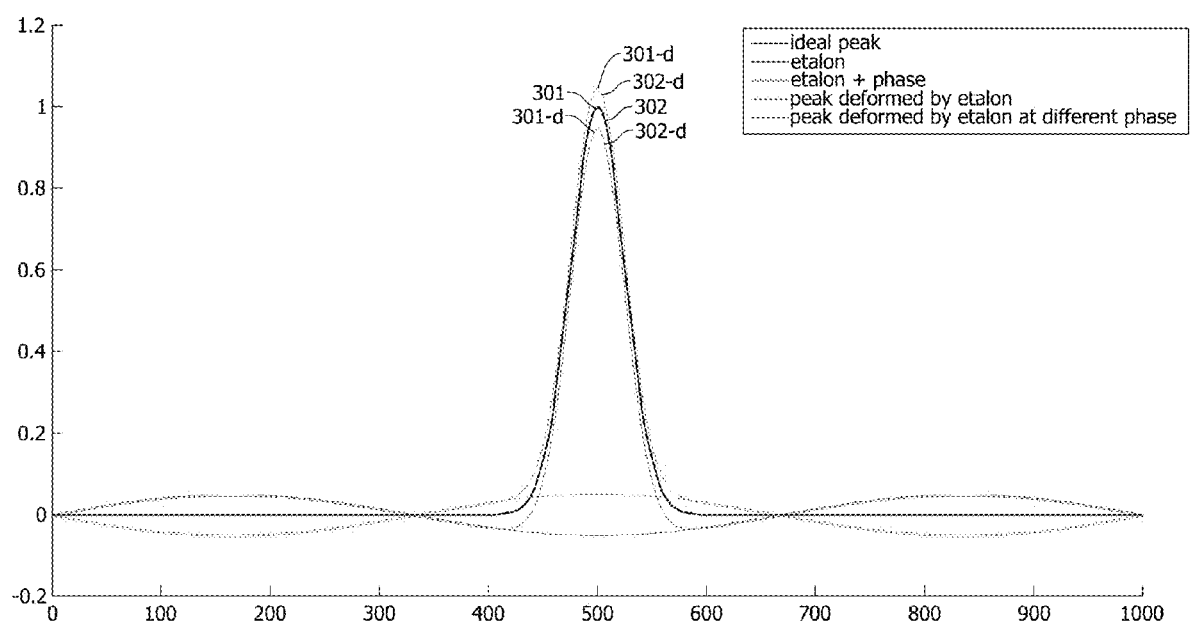
FIG. 3 shows effects of etalons on measurements of gases.

The absorption spectra of gases, however, are affected by etalons, which are caused by overlapping laser lights. Etalons may have sinusoidal waveforms. FIG. 3 is a plot of exemplary spectra showing the effects of etalons on absorption spectra. When laser light travels back and forth between parallel or quasi-parallel surfaces, the laser light and its reflection interfere with one another, creating sinewave in the absorption spectra. As a result, an absorption peak 301 and a spectrum 302 of the gas are deformed by the etalons into peaks 301-d and spectra 302-d.

Figure 4A:
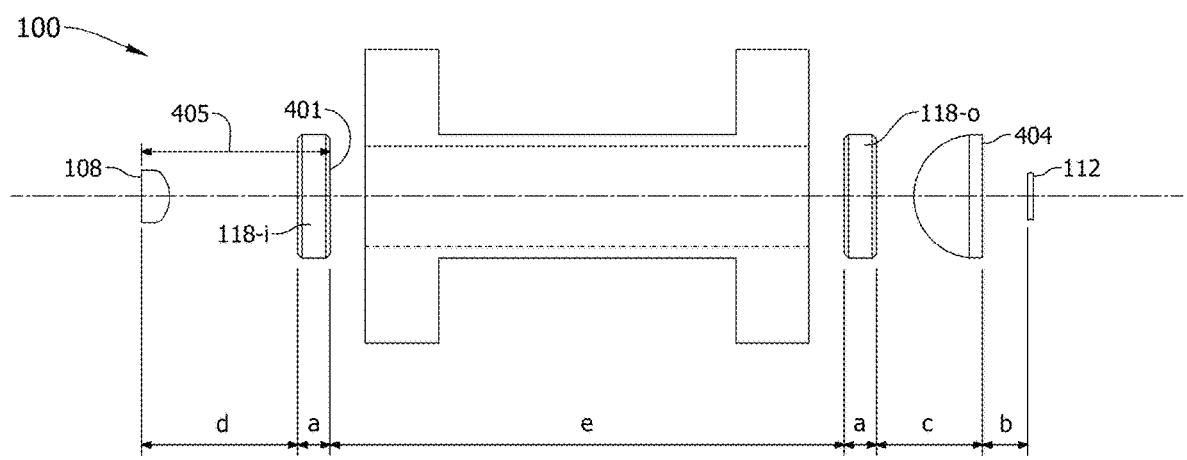
FIG. 4A is a simplified diagram of optical components of the system shown in FIG. 1.
Figures 4B, 4C:
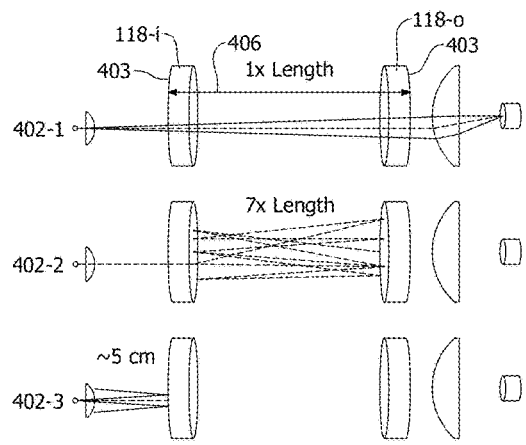
FIG. 4B shows formation of etalons.
FIG. 4C is a table listing etalons.
Figure 4D:
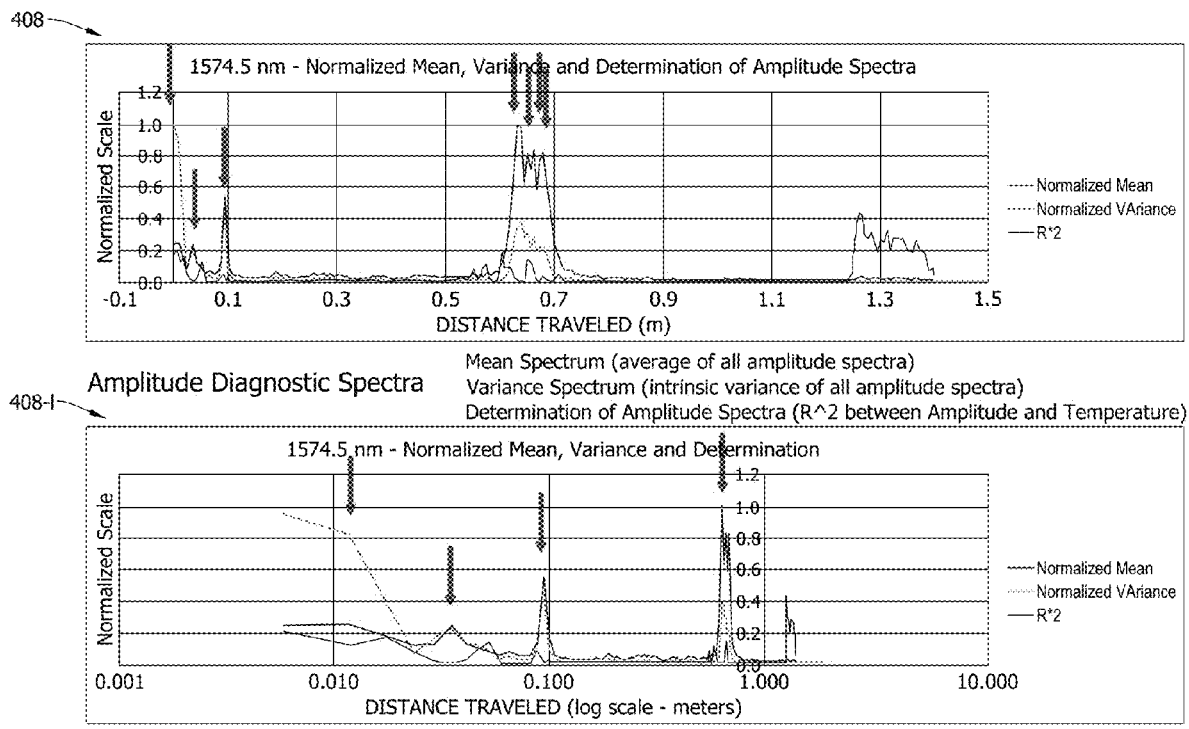
FIG. 4D shows amplitude spectra with the input laser at a wavelength of 1574.5 nm.

FIGS. 4A-4D show the formation and effects of etalons in further details. FIG. 4A is a simplified diagram of optical components of system 100. FIG. 4B shows three etalons 402-1, 402-2, 402-3, which are major contribution of system noise. FIG. 4C is a table listing significant etalons. FIG. 4D shows the mean, variance, and amplitude/power spectra of etalons obtained by applying a Fourier transform to raw absorption spectra. The input light is at a wavelength of 1574.5 nm. Optical components of system 100 include collimator 108, input mirror 118-i, output mirror 118-o, a collecting lens 404, and photodetector 112 (FIG. 4A). Etalon 402-1 may occur when light 202 travels one length (L) 406 of optical cavity 122. Cavity length 406 is the distance between outer side 403 of input mirror 118-i and outer side 403 of output mirror 118-o (FIG. 4B). Etalon 402-2 may occur after the light has travelled across output mirror 118-o and reentered back as re-entrant. Etalon 402-2 typically occurs after light has travelled seven times of cavity length 406. Etalon 402-3 may occur when light reflected back to collimator 108. FIG. 4C lists most significant etalons. FIG. 4D shows plot 408, 408-1 depicting the mean, variances, and amplitude spectra of etalons. In plot 408-1, the x-axis of the distance travelled is in a logarithmic scale. As shown, etalons 402-1, 402-2, 402-3 are disruptive in the measurements of gas absorption spectra. Although system 100 involves hundreds or thousands of reflections within optical cavity 122 for a single measurement, the first several reflections contribute disproportionally to self-interference noise because the light beam has not diverged significantly at the early travel time. The most disruptive etalons are those associated with optical distances between optical surfaces that produce interfering sine waves with a semi-period, or a half of the period, equivalent in dimension to be within the absorption bandwidth at half-height of the gases of interest, e.g., 402-3. Etalon 402-3 is more disruptive than other etalons 402-1 and 402-2 because etalon 402-3 affects absorption peaks of gases of interest more than other etalons, reducing measurement accuracy and precision.

In known ICOS systems, etalons are mitigated using piezo-electric actuators placed on input and/or output mirrors to modulate the cavity dimensions at a frequency vastly different from the laser scanning frequency. The known approach, however, is complicated and expensive. Further, because etalons move in phase and amplitude as temperature varies, known systems and methods would need to be designed, redesigned, or adjusted to take into consideration of the effects of temperature on etalons, increasing complexity and costs of known systems. In addition, the known approach is designed for a system input with a laser at a single nominal wavelength.

Systems and methods described herein overcome the above described problems in known systems and methods. A plurality of lasers may be used in system 100 such that multiple gases are analyzed by one system 100, instead of multiple ICOS systems. A reflective collimation mirror may replace a collimation lens to reduce etalons and increase the performance with a plurality of lasers. Parameters of system 100, such as a radius of curvature of input mirror 118-i, the cavity length, the divergence angle of the injected laser beam, the launch angle of the laser beam, and the launch distance of the laser beam, may be adjusted to select optimized parameters with etalons reduced or minimized. A GRIN lens may be used in collimator 108 to reduce etalons. The parameters may be adjusted separately or jointly in any combination. System 100 may include one or more features described herein in any combination. For example, a collimation lens may be used and one or more parameters of system 100 are adjusted.

Figure 5A:
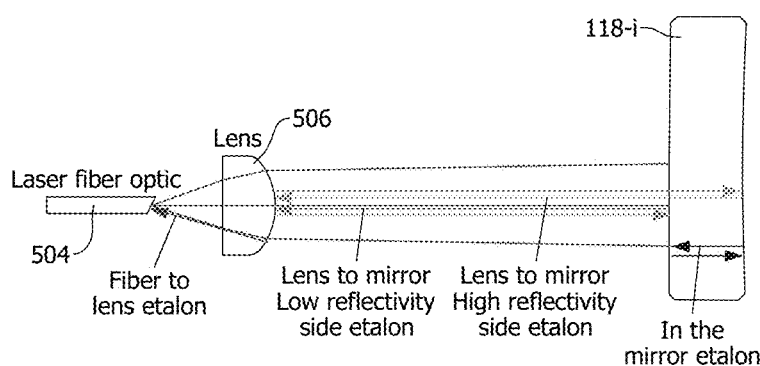
FIG. 5A shows light trajectories when a lens is used as a collimator.
Figure 5B:
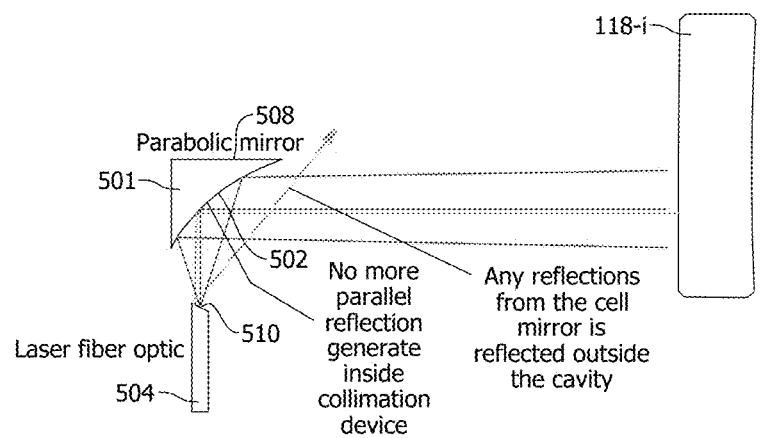
FIG. 5B shows light trajectories when a reflective collimation mirror is used.

In some embodiments, collimator 108 includes reflective collimation mirror 501 (FIG. 5B). Reflective collimation mirror 501 has a reflective surface 502. The reflectance of reflective surface 502 may be greater than 96%. Reflective surface 502 may be coated with metal. Reflective surface 502 is parabolic or being a segment of a paraboloid. In one example, the end surface of optic fiber 504 that faces reflective collimation mirror 501 is angled, where an end surface 510 of optic fiber 504 forms a non-90° angle with optic fiber 504 in the length direction.

FIGS. 5A and 5B provide a comparison between a collimation lens 506 and a reflective collimation mirror 501. Because of parallel or quasi-parallel surfaces between laser optic fiber 504, collimation lens 506, and input mirror 118-i, etalons caused by the parallel or quasi-parallel surfaces may include fiber to lens etalons, lens to mirror low reflectivity side etalons, lens to mirror high reflectivity side etalons, and mirror etalons. When a reflective collimation mirror 501 replaces collimation lens 506, the number of parallel or quasi-parallel surfaces between laser optic fiber 504 and reflective collimation mirror 501 or between reflective collimation mirror 501 and input mirror 118-i is significantly reduced. Parallel refection inside collimation lens 506 does not occur with reflective collimation mirror 501. Reflections from input mirror 118-i are reflected away or outside of gas cell 116. Surfaces 508 of reflective collimation mirror 501, including reflective surface 502, and end surface 510 of optic fiber 504 are angled in such a way that light does not return on the same path. All of the changes lead to reduction of etalons.

A reflective collimation mirror 501 is advantageous when a plurality of lasers at different wavelengths are used. Because reflective collimation mirror 501 reflects light, unlike in collimation lens 506, which also refracts light, chromatic aberration does not occur with reflective collimation mirror 501 due to effects of wavelength on refraction but similar reflectance over wavelengths due to metallic coating versus anti-reflection coating in collimation lens 506. Therefore, one single reflective collimation mirror 501 may be used in system 100 having lasers in a plurality of nominal wavelengths.

Having one single reflective collimation mirror 501 in system 100 having lasers in a plurality of nominal wavelengths is advantageous for additional reasons. Replacing collimation lens 506 with reflective collimation mirror 501 shortens the overall length of the spectrometer assembly, enabling a compact configuration. Further, a single laser launch assembly may be used for a plurality of lasers, instead of using two or more laser launch assemblies, thereby simplifying the optomechanical assembly. Using reflective collimation mirror 501 also reduces cost by reducing the number of parts needed in system 100 and reducing the time and labor in manufacturing, quality control, and service because only one beam alignment is needed, instead of two or more beam alignment being needed in a typical system. Moreover, reflective collimation mirror 501 reduces effects of wavelengths on the travel paths of light from the plurality of lasers, thereby simplifying the measurements of a plurality of gases using one ICOS system.

In some embodiments, collimator 108 is a GRIN lens. A GRIN lens has a gradient profile such that a refractive index of the lens varies in a direction perpendicular to the optical axis of the lens. In an embodiment, the refractive index varies according to the following equation:

$$N = N_0 \left[1 - \left(\frac{k}{2}\right) r^2 \right], \quad \text{(Eq. 1)}$$

where $N_0$ is a base refractive index corresponding to the center of the lens, k is a gradient constant, and r is a radius variable that represents a distance from the center of the lens. In one embodiment, the GRIN lens is cylindrical, with a diameter in a range between 0.5 mm and 3 mm, which is smaller than a diameter of conventional spherical or aspheric lenses (e.g., plano-convex or bi-convex) that may start at 5 mm or more in diameter. For example, it may be difficult to grind, polish, or mold from a polymer material a spherical or aspheric lens at small sizes with an appropriate focal length. Further, conventional spherical or aspheric lens below, e.g., 5 mm in diameter, may not be available commercially at a low cost or produced without custom equipment. In contrast, a GRIN lens that is commonly commercially available at a low cost may be approximately 1.0 mm in diameter.

Use of a GRIN lens instead of a typical spherical or aspherical refractive lens reduces etalons. A GRIN lens has a smaller size than a typical spherical or aspherical refractive lens, thereby reducing the initial beam size entering into optical cavity 122 and in turn reducing etalons.

Figure 6A:
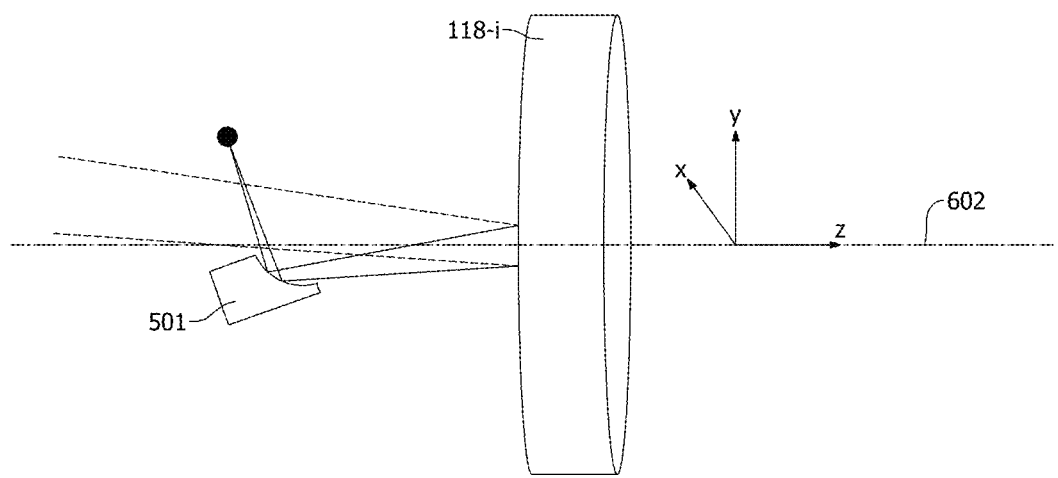
FIG. 6A shows an exemplary arrangement of an angled collimator.
Figure 6B:
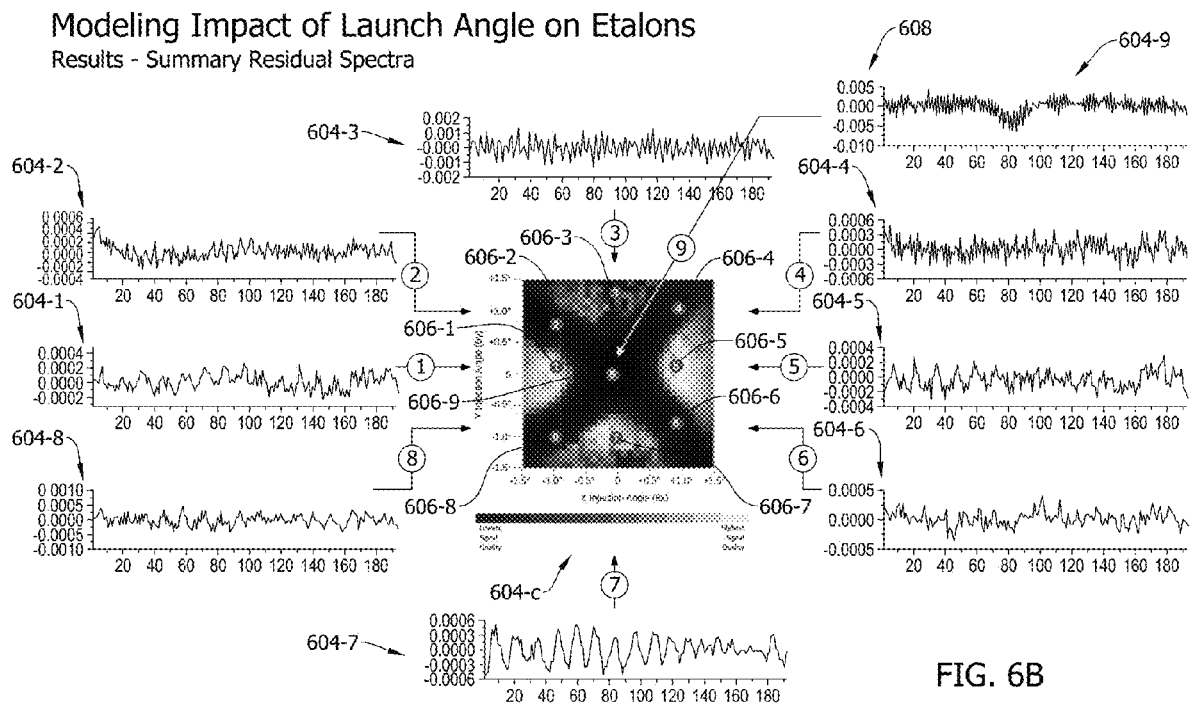
FIG. 6B shows effects of launch angles of a laser on etalons.

In the exemplary embodiment, the launch angle of light into gas cell 116 may be adjusted. FIG. 6A show an exemplary arrangement of system 100. Collimator 108 is at an angle with input mirror 118-i. Although a reflective collimation mirror 501 is depicted in FIG. 6A, adjusting the launch angle as described herein may be applied to system 100 having a collimation lens 506 or GRIN lens. FIG. 6B shows effects of a launch angle on etalons. A launch angle or an injection angle is the angle of the incident or impinging laser into optical cavity 122. Light into optical cavity 122 may be assumed to have a Gaussian profile. A launch angle is calculated as the maximum laser intensity direction relative to z-axis 602 of optical cavity 122. A z-axis of an optical cavity is the optical axis of cavity mirrors 118 or the centerline of optical cavity 122. A launch angle may be represented as a pair of angles θx and θy, which are angles at which the light is tilted toward x-axis or y-axis, respectively. x-axis and y-axis are axes orthogonal to one another and to z-axis 602 of optical cavity 122 (see FIG. 6A). FIG. 6B is based on data of system 100 having a reflective collimation mirror 501 and acquired with zero gas, which includes dry nitrogen ($N_2$). Zero gas does not absorb light and therefore measurements from detector 112 are system noise, such as etalons. Plots 604-1-604-9 are residual spectra at nine different launch angles 606-1-606-9. Residual spectra are calculated as the algebraic differences or point by point differences between a raw gas absorption (GA) spectrum, calculated as GA=(I/$I_o$)−1, and a fitted or ideal GA scale spectrum of the gas in gas cell 116. In plots 604-1-604-9, the x-axis is wavelength and y-axis is the amplitude of the residual spectra. Plot 604-c shows signal quality, including but limited to signal to noise ratio (SNR), of system 100 as a function of launch angle 606. The signal quality is color coded, with black indicating poorest signal quality while white indicating highest signal quality. The x- and y-axes of plot 604-c are θx and θy angles in degrees, with center being zero, where the light is on-axis alignment with z-axis 602 (FIG. 6A).

As shown in FIG. 6B, negative effects of etalons increase when amplitude 608 of etalons increases, which are the y-axis values in plots 604-1-604-9. Negative effects of etalons increase when the signal quality reduces (the dark regions in plot 604-c). Negative effects of etalons also increase when the semi-period of the etalons is within the range half height bandwidth of the gas absorption bandwidth or approximate to the half height bandwidth range such as within the range of third or quarter height bandwidth of the gas absorption bandwidth (plot 604-7). Based on the amplitude and period/frequency of etalons, among spectra 5, 8, and 9, spectrum 5 (plot 604-5) is marked as best while spectra 8 and 9 (plot 604-8, 604-9) are marked as poor or worst, respectively. Angle 606-5 has a θx angle of 1.0° and θy of 0. Launch angle 606-9 corresponds to angle zero, where launch angle 606 is on axis. Although in plot 604-7 the signal quality is relatively good and the amplitudes of etalons are relatively low, the setup with angle 606-7 (plot 604-7) produces disruptive exterior cavity elations that have a semi-period within or approximate the half-heigh bandwidth of absorption spectra (see etalons 402-3 in FIG. 4B), and should be avoided.

In operation, launch angle 606 may be selected based on the residual spectra when the sample gas is dry nitrogen. Launch angle 606 is varied and residual spectra are collected for each launch angle 606. An optimized launch angle is selected as a launch angle corresponding to residual spectra having the lowest amplitude and/or semi-period of the etalons not being within a predetermined threshold such as a half-height bandwidth, a third- or quarter-height bandwidth of the gas absorption bandwidth, or any other range as determined by the measurement precision requirements.

When system 100 has a plurality of lasers at different nominal wavelengths, a reflective collimation mirror 501 is advantageous over a collimation lens 506. Because reflection is usually equal for different wavelengths, a single launch angle may be optimized for different wavelengths in system 100 that includes reflective collimation mirror 501.

Figure 7A:
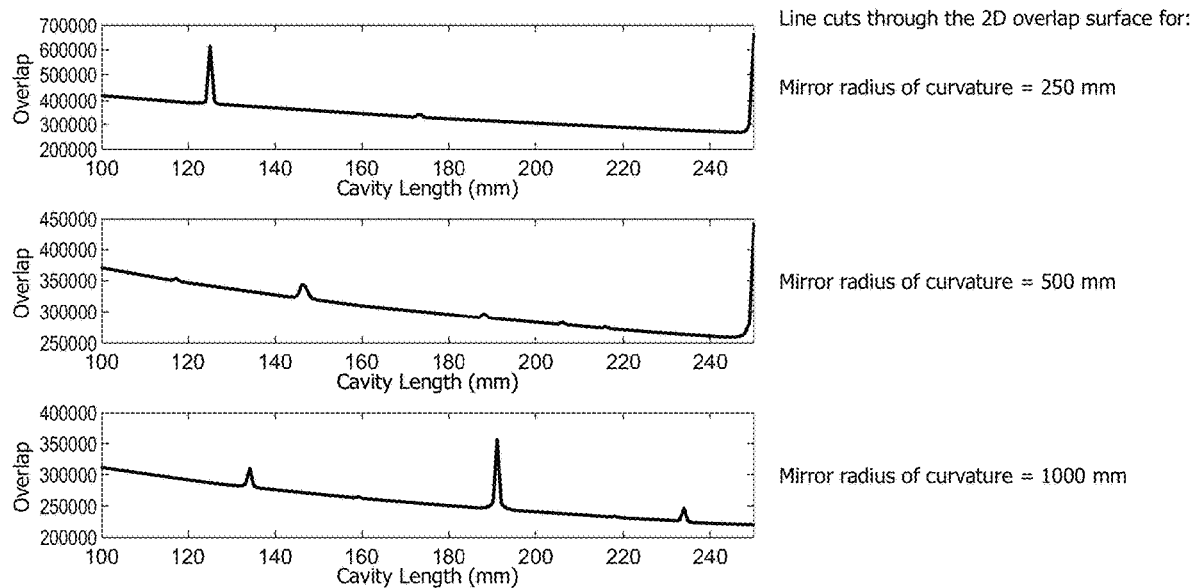
FIG. 7A shows effects of a radius of curvature and cavity length on etalons.
Figure 7B:
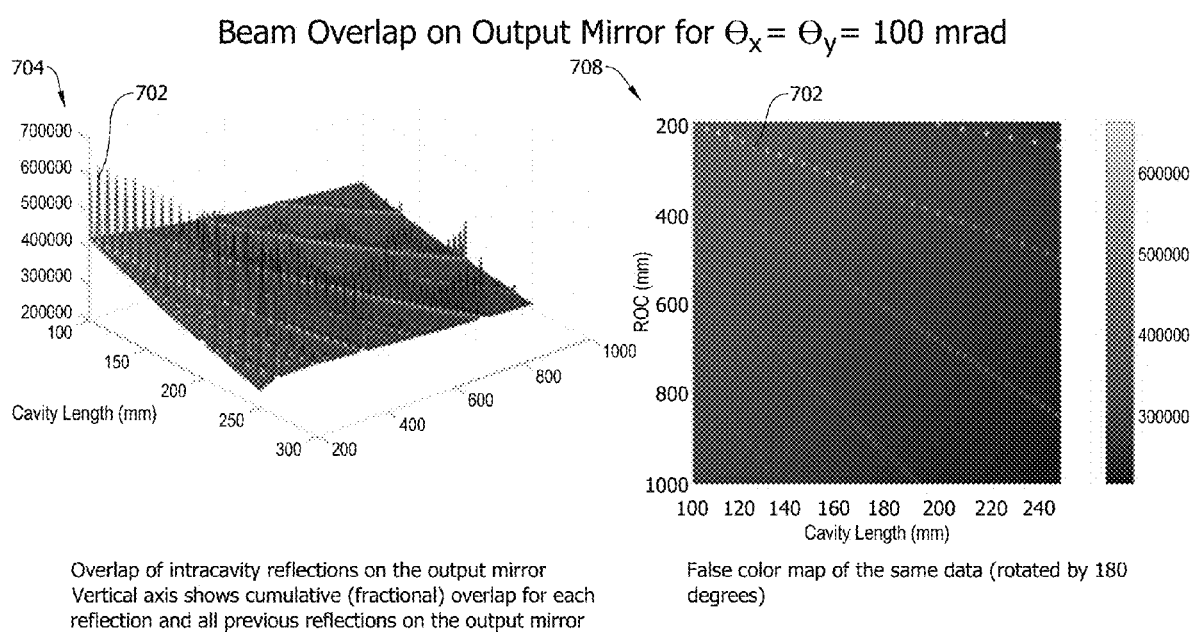
FIG. 7B shows effects of a radius of curvature and cavity length on etalons in 3D plots.

In the exemplary embodiment, radius of curvature of cavity mirror 118 and cavity length 406 may be jointly adjusted to reduce etalons. As used herein, a radius of curvature of cavity mirror 118 is the radius of curvature of inner side 401 of cavity mirror 118 (see FIGS. 8B and 8C described later). FIGS. 7A and 7B show beam overlaps inside optical cavity 122 as a function of radius of curvature of cavity mirror 118 and cavity length 406 when launch angles θx and θy are 100 milliradian (mrad), based on computer simulation data. Beam overlaps cause etalons. FIG. 7A shows beam overlaps as a function of cavity length 406 for a radius of curvature of cavity mirror 118 at 250 mm, 500 mm, or 1000 mm, respectively. The y-axis is in an arbitrary unit. FIG. 7B shows three dimensional (3D) plots (plot 704 and a false color map 708) of the results. Beam overlap peaks 702 are shown as dots in false color map 708. In operation, a pair of radius of curvature and cavity length may be selected as a pair that does not correspond to a beam overlap peak 702. A look-up table may be generated by listing beam overlap peaks and corresponding pairs of a radius of curvature and cavity length based on the 3D plot 704 or false color map 708. A radius of curvature and/or cavity length may be selected by avoiding pairs listed in the look-up table.

Figure 8A:
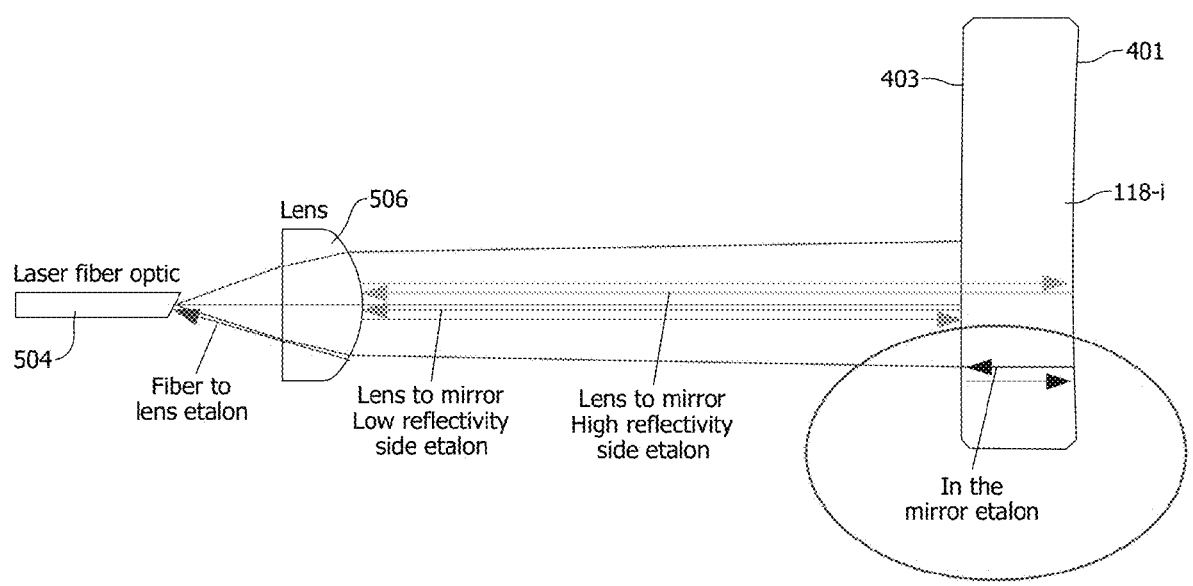
FIG. 8A shows formation of mirror etalons.
Figure 8B:
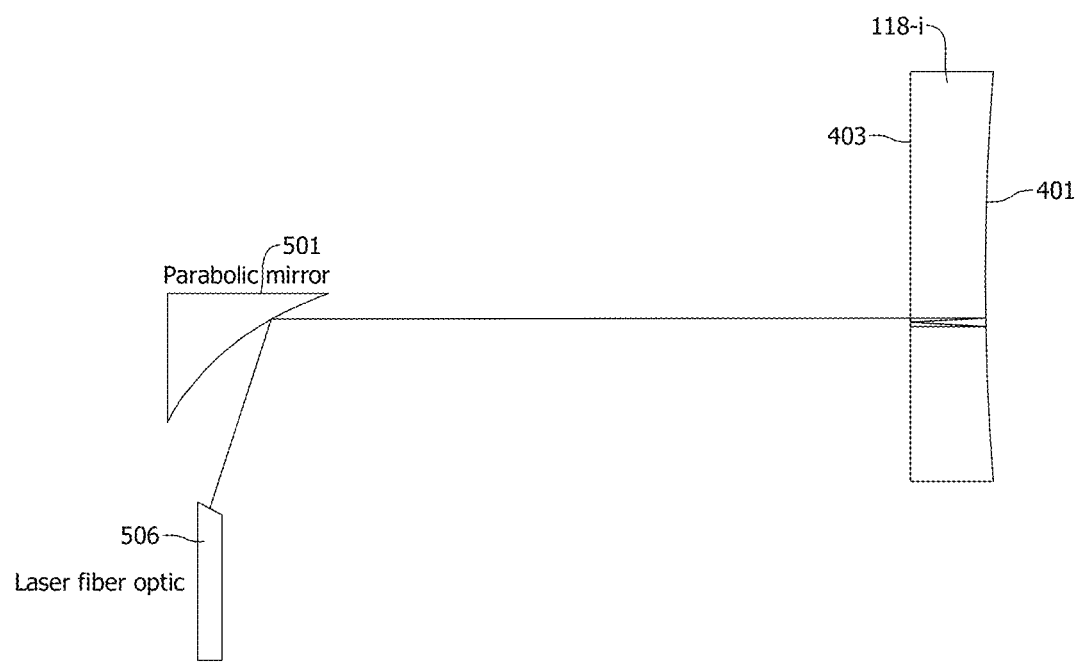
FIG. 8B shows light trajectories.
Figure 8C:
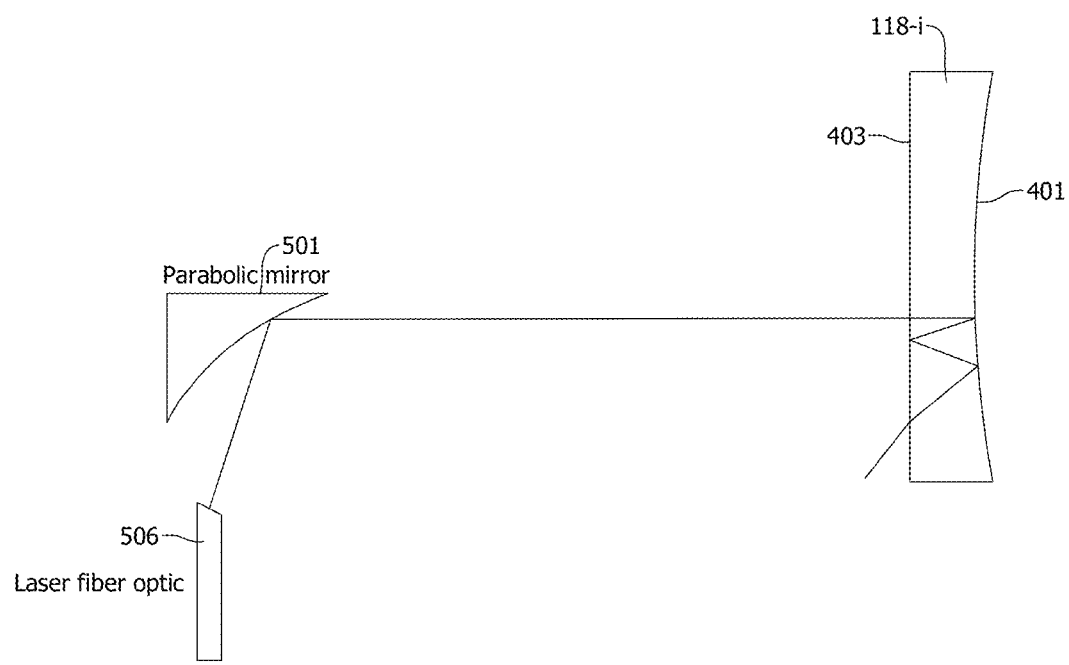
FIG. 8C shows light trajectories when a radius of curvature of the input mirror is reduced.
Figure 8D:
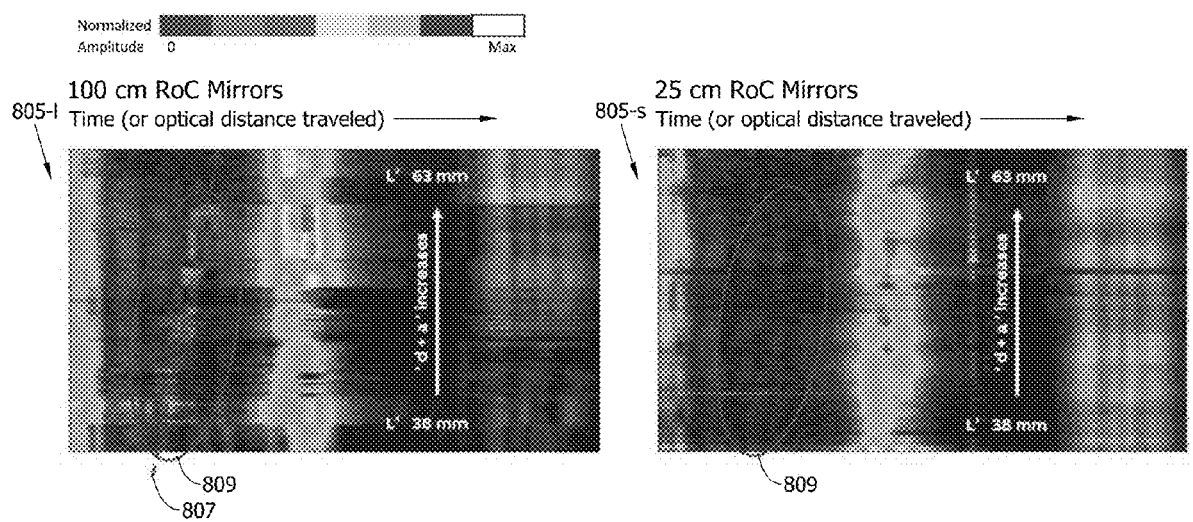
FIG. 8D shows effects on etalons from the radius of curvature of the input mirror.

FIGS. 8A-8D show effects of a radius of curvature of cavity mirror 118 alone on etalons. A reduced radius of curvature has reduced etalons. FIGS. 8A and 8B shows etalons occur when light is reflected back and forth between two sides of input mirror 118-i. When a radius of curvature reduces, inner side 401 of input mirror 118-i is less parallel with outer side 403 of input mirror 118-i (FIG. 8C). As a result, etalons are reduced. FIG. 8D shows a comparison of etalons when the radius of curvature is 100 cm (plot 805-1) versus when the radius of curvature is 25 cm (plot 805-s). The x-axis of plots 805-1, 805-s are the travel time or optical distance travelled. The y-axis is the distance between the collimator 108 and input mirror 118-i. Spectra were collected continuously while the distance between collimator 108 and input mirror 118-i was slowly increased. The amplitude spectrum obtained by applying a Fourier transform to the residual spectra of zero gas is depicted as color maps in FIG. 8D. As shown in FIG. 8D, when using an input mirror having a 100 cm radius of curvature, etalons are observed as marked by a dotted line 807 in an area 809. In contrast, when using an input mirror having a 25 cm radius of curvature, etalons are not observed at the same area 809. The radius of curvature of output mirror 118-o may be the same as the radius of curvature of input mirror 118-i and may be adjusted at the same time.

Figure 9:
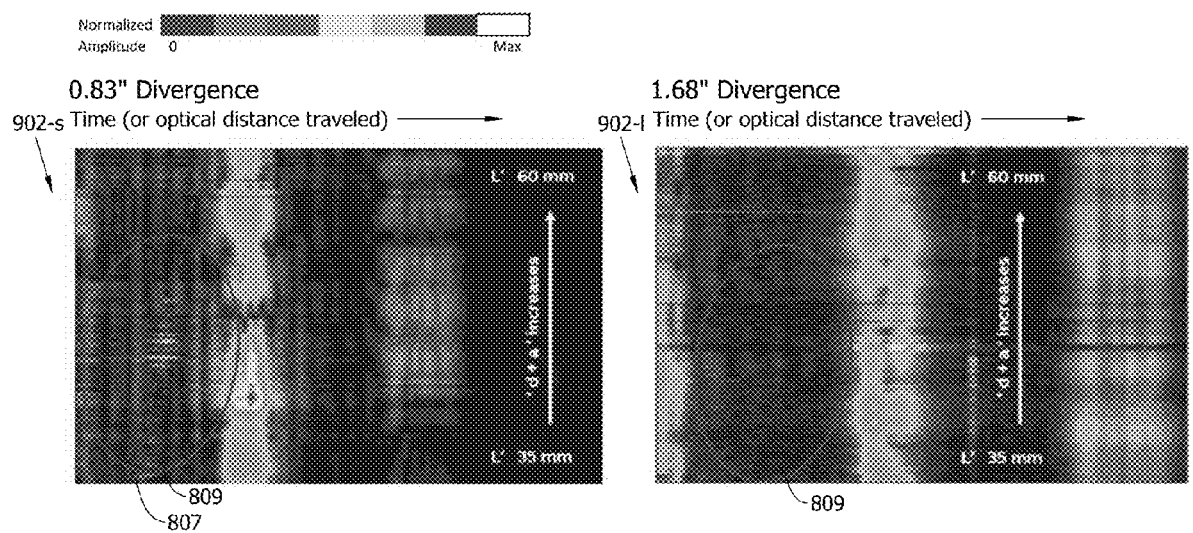
FIG. 9 shows effects on etalons from divergence angles of collimator.

FIG. 9 shows effects of divergence angles of injected laser beam on etalons. A divergence angle of a laser beam is the angle that the laser light beam diverges. The divergence angle of a laser beam is affected by the divergence angle of collimator 108, which is the angle of light diverging from the collimator. The divergence angle of a laser beam may be changed by changing collimator 108 with a different divergence angle. FIG. 9 shows plots 902-s, 902-1 of etalons as a function time or optical distance traveled in the x-axis and a distance between collimator 108 and input mirror 118-i in the y-axis. The amplitude spectrum obtained by applying a Fourier transform to the residual spectra of zero gas is depicted as color maps in FIG. 9. The color maps indicate the level of etalons. As shown, when the divergence angle of collimator 108 is 0.83°, etalons are observed as marked by dotted line 807 in area 809 (plot 902-s). In contrast, when the divergence angle of collimator 108 is 1.68°, etalons are not observed in the same area 809 (plot 902-1). Accordingly, an increase of divergence angle of collimator 108 reduces etalons.

Figure 10A:
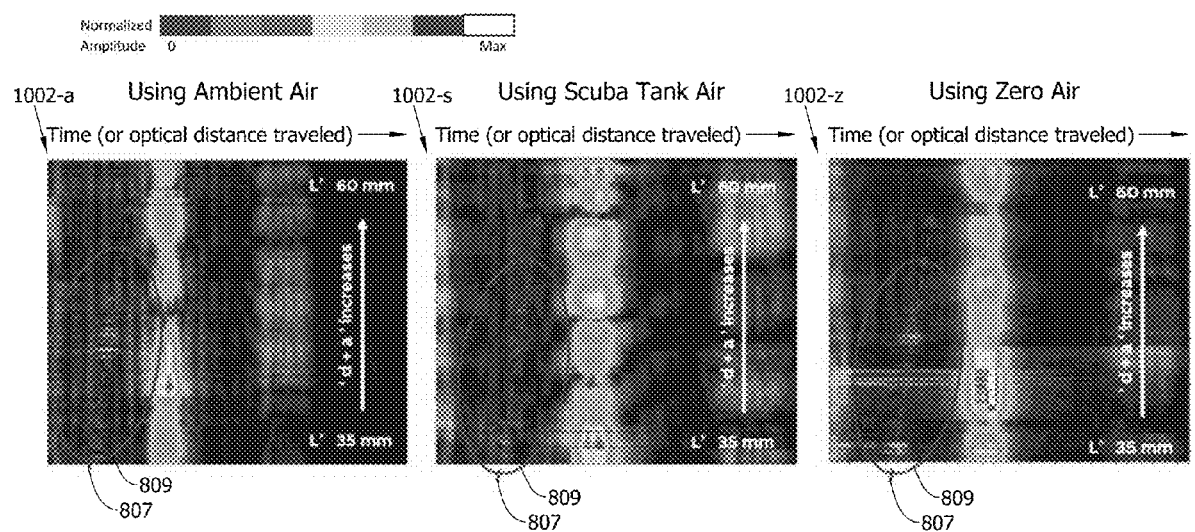
FIG. 10A shows effects on etalons from launch distances of laser.
Figure 10B:
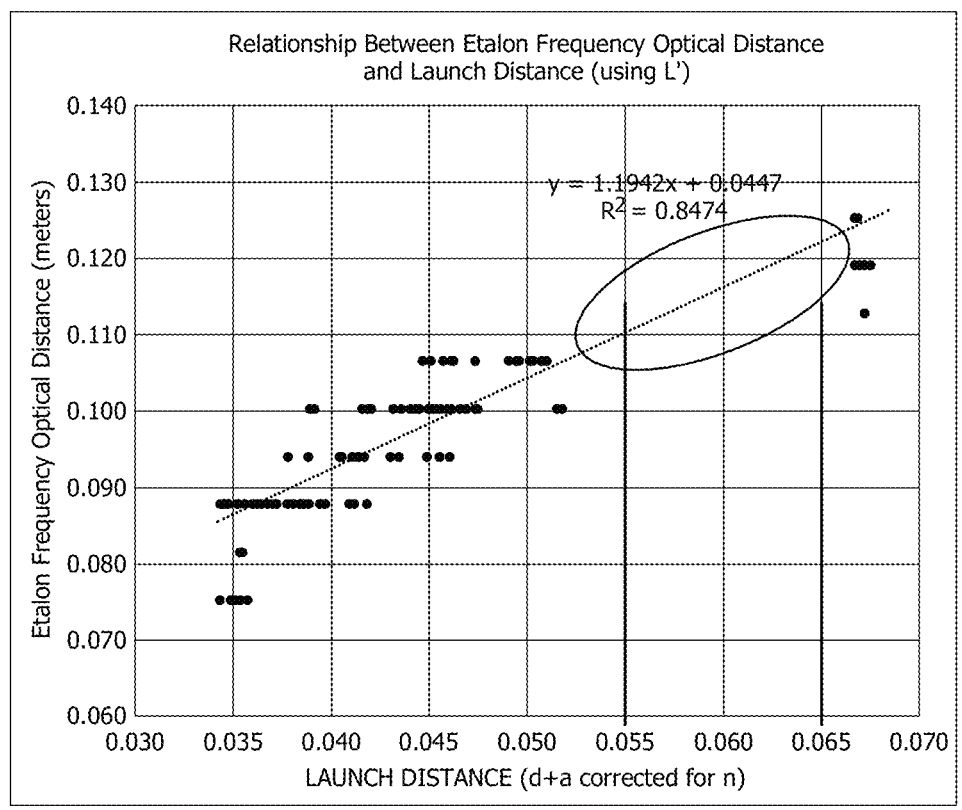
FIG. 10B shows relationship between etalon frequency optical distances and launch distances.

FIGS. 10A and 10B show effects of launch distances on etalons. As used herein, a launch distance is the distance between the collimator 108 and the inner side 401 of the inner mirror 118-i (distance 405 in FIG. 4A). FIG. 10A shows amplitude spectra obtained by applying a Fourier transform to the residual spectra of etalons measured using ambient air (plot 1002-a), scuba tank air (plot 1002-s), and zero gas (plot 1002-z). FIG. 10B is a plot of etalon frequencies as a function of launch distance. The data was acquired using cavity mirrors having a 100 cm radius of curvature and a divergence angle of 0.83° for the injected beam. As shown in FIG. etalons are observed as marked by dotted line 807 in area 809. Amplitudes of etalons are negligible when the launch distance is between 55 mm and 65 mm.

In operation, to select an optimized range of launch distance, residual spectra are collected while varying the launch distance. The residual spectra or etalon amplitude may be plotted as a function of the launch distance. An optimized launch distance or an optimized range of launch distances may be selected based on the plot. For example, the optimized launch distance or optimized range of launch distance is selected as the launch distance corresponding to the amplitude of etalons being less than a predetermined threshold such as the minimum amplitude, within 10% above the minimum amplitude, within 15% above the minimum amplitude, or any threshold as determined by the system requirements or specification.

The values of launch angles, launch distances, divergence angles, radii of curvature, or cavity lengths provided above are examples only and specific to a particular configuration of an ICOS assembly. The values may change with optomechanical configurations of the ICOS assembly.

Figure 11:
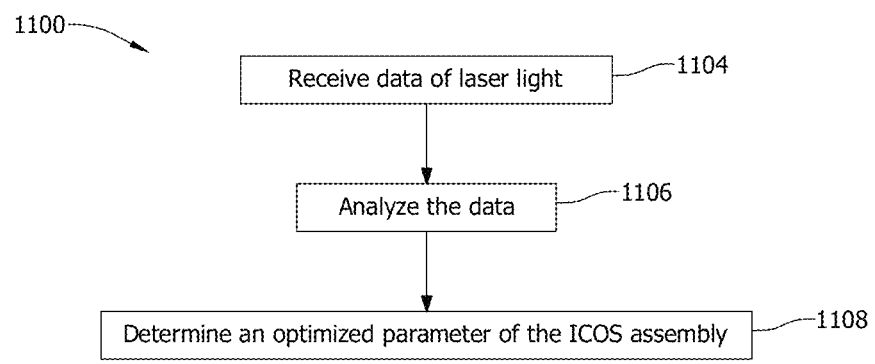
FIG. 11 is a flow chart of an exemplary method.

FIG. 11 is an exemplary method 1100 of calibrating parameters of an ICOS assembly. The ICOS assembly may be the ICOS assemblies described above. Method 1100 may be implemented with calibration computing device 114. Method 1100 includes receiving 1104 data of laser light. The data may be simulated data or data collected by detector 112. Data may be simulated or collected while varying parameters of ICOS assembly. One or more parameters may be varied at one time. Method 1100 further includes analyzing 1106 the data. In addition, method 1100 includes determining 1108 an optimized parameter or an optimized range of the parameter of the ICOS assembly. The parameter(s) may be optimized by minimizing or reducing noise to be below a predetermined threshold, or selecting the parameter(s) among the tested parameter(s) corresponding to the smallest level of noise. Noise may be noise from etalons.

Figure 12:
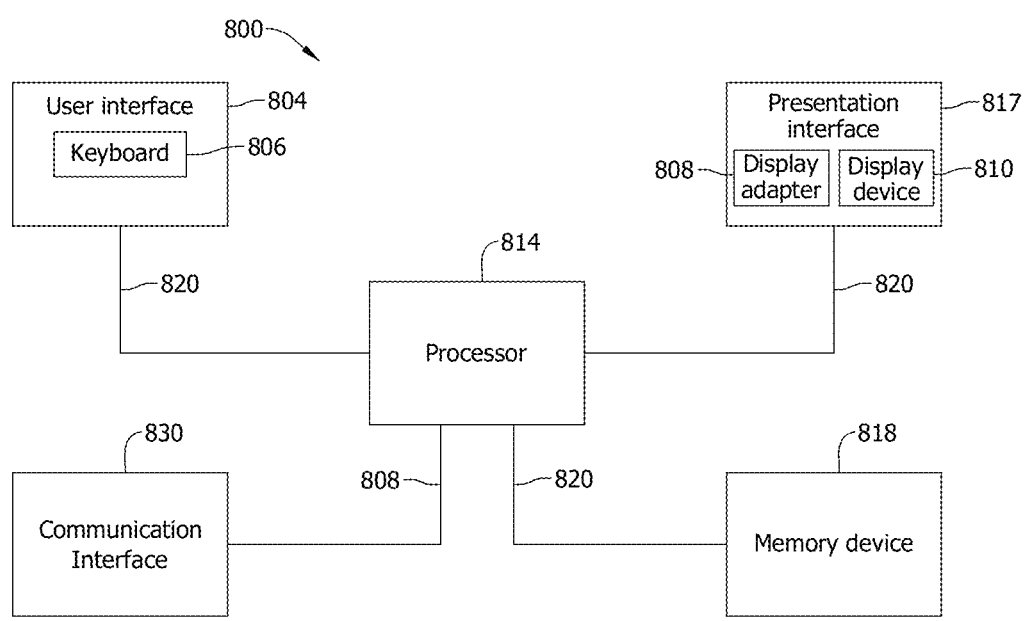
FIG. 12 is a block diagram of an exemplary computing device.

Calibration computing device 114 described herein may be any suitable computing device 800 and software implemented therein. FIG. 12 is a block diagram of an exemplary computing device 800. In the exemplary embodiment, computing device 800 includes a user interface 804 that receives at least one input from a user. User interface 804 may include a keyboard 806 that enables the user to input pertinent information. User interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a presentation interface 817 that presents information, such as input events and/or validation results, to the user. Presentation interface 817 may also include a display adapter 808 that is coupled to at least one display device 810. More specifically, in the exemplary embodiment, display device 810 may be a visual display device, such as a cathode ray tube (CRT), a liquid crystal display (LCD), a light-emitting diode (LED) display, and/or an "electronic ink" display. Alternatively, presentation interface 817 may include an audio output device (e.g., an audio adapter and/or a speaker) and/or a printer.

Computing device 800 also includes a processor 814 and a memory device 818. Processor 814 is coupled to user interface 804, presentation interface 817, and memory device 818 via a system bus 820. In the exemplary embodiment, processor 814 communicates with the user, such as by prompting the user via presentation interface 817 and/or by receiving user inputs via user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 818 includes one or more devices that enable information, such as executable instructions and/or other data, to be stored and retrieved. Moreover, memory device 818 includes one or more computer readable media, such as, without limitation, dynamic random access memory (DRAM), static random access memory (SRAM), a solid state disk, and/or a hard disk. In the exemplary embodiment, memory device 818 stores, without limitation, application source code, application object code, configuration data, additional input events, application states, assertion statements, validation results, and/or any other type of data. Computing device 800, in the exemplary embodiment, may also include a communication interface 830 that is coupled to processor 814 via system bus 820. Moreover, communication interface 830 is communicatively coupled to data acquisition devices.

In the exemplary embodiment, processor 814 may be programmed by encoding an operation using one or more executable instructions and providing the executable instructions in memory device 818. In the exemplary embodiment, processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Figure 13:
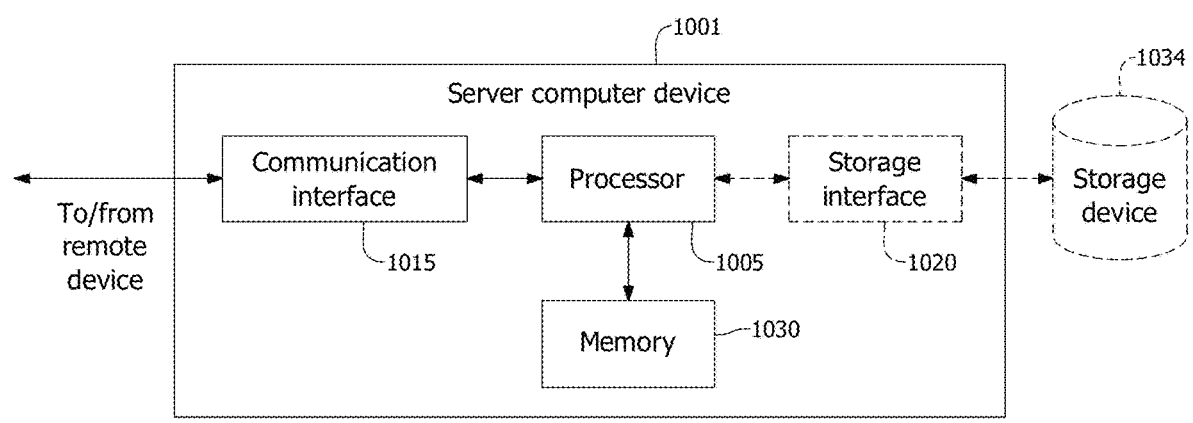
FIG. 13 is a block diagram of an exemplary server computing device.

FIG. 13 illustrates an exemplary configuration of a server computer device 1001 such as calibration computing device 114. Server computer device 1001 also includes a processor 1005 for executing instructions. Instructions may be stored in a memory area 1030, for example. Processor 1005 may include one or more processing units (e.g., in a multi-core configuration).

Processor 1005 is operatively coupled to a communication interface 1015 such that server computer device 1001 is capable of communicating with a remote device or another server computer device 1001. For example, communication interface 1015 may receive data from calibration computing device 114, via the Internet.

Processor 1005 may also be operatively coupled to a storage device 1034. Storage device 1034 is any computer-operated hardware suitable for storing and/or retrieving data, such as, but not limited to, wavelength changes, temperatures, and strain. In some embodiments, storage device 1034 is integrated in server computer device 1001. For example, server computer device 1001 may include one or more hard disk drives as storage device 1034. In other embodiments, storage device 1034 is external to server computer device 1001 and may be accessed by a plurality of server computer devices 1001. For example, storage device 1034 may include multiple storage units such as hard disks and/or solid state disks in a redundant array of inexpensive disks (RAID) configuration. storage device 1034 may include a storage area network (SAN) and/or a network attached storage (NAS) system.

In some embodiments, processor 1005 is operatively coupled to storage device 1034 via a storage interface 1020. Storage interface 1020 is any component capable of providing processor 1005 with access to storage device 1034. Storage interface 1020 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 1005 with access to storage device 1034.

At least one technical effect of the systems and methods described herein includes (a) injecting a plurality of laser light at a plurality of wavelength ranges; (b) a reflective collimation mirror; (c) a plurality of pumps; (d) adjustments of system components to reduce etalons; and (e) a GRIN lens.

Exemplary embodiments of systems and methods of measuring contaminants are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A laser absorption spectrometry system for gas measurement, comprising:
an integrated cavity output spectroscopy (ICOS) assembly comprising:
a gas cell comprising a cell body defining an optical cavity;
one or more tunable diode lasers having one or more nominal wavelengths; and
a reflective collimation mirror positioned in an optical path between the one or more tunable diode lasers and the gas cell, the reflective collimation mirror configured to reduce noise from etalons, wherein when light travels back and forth between parallel surfaces and/or quasi-parallel surfaces in the optical path, the light and its reflection interfere with one another and cause the etalons, the etalons introducing the noise in absorption spectra of the light by gases in the gas cell,
wherein the one or more tunable diode lasers comprise a first tunable diode laser configured to emit first laser light in a wavelength range corresponding to a first contaminant in the gases and a second tunable diode laser configured to emit second laser light in a wavelength range corresponding to a second contaminant in the gases.

2. The system of claim 1, wherein the reflective collimation mirror has a parabolic reflection surface.

3. The system of claim 1, wherein the one or more tunable diode lasers include a first tunable diode laser configured to emit first laser light in a first wavelength range in a vicinity of 1574.5 nm.

4. The system of claim 1, wherein the one or more tunable diode lasers include a first tunable diode laser configured to emit first laser light in a wavelength range corresponding to an absorption range of $H_2S$ and $CO_2$.

5. The system of claim 1, wherein the one or more tunable diode lasers include a second tunable diode laser configured to emit second laser light in a second wavelength range in a vicinity of 1314 nm.

6. The system of claim 1, wherein the one or more tunable diode lasers include a second tunable diode laser configured to emit second laser light in a second wavelength range corresponding to an absorption range of $H_2O$.

7. The system of claim 1, wherein the one or more tunable diode lasers include a third tunable diode laser configured to emit third laser light in a third wavelength range in a vicinity of 760 nm.

8. The system of claim 1, wherein the one or more tunable diode lasers include a third tunable diode laser configured to emit third laser light in a third wavelength range corresponding to an absorption range of $O_2$.

9. A laser absorption spectrometry system for gas measurement, comprising:
an integrated cavity output spectroscopy (ICOS) assembly comprising:
a gas cell comprising a cell body defining an optical cavity;
three or more tunable diode lasers having three or more nominal wavelengths and configured to emit three or more laser light in three or more wavelength ranges, the three or more wavelength ranges corresponding to absorption ranges of three or more different contaminants in gases; and
a combiner configured to multiplex the three or more laser light into a combined laser light configured to be coupled into the optical cavity, the combined laser light having the three or more wavelength ranges,
wherein the ICOS assembly further comprises a reflective collimation mirror positioned in an optical path between the three or more tunable diode lasers and the gas cell, the reflective collimation mirror configured to reduce noise from etalons, wherein when light travels back and forth between parallel surfaces and/or quasi-parallel surfaces in the optical path, the light and its reflection interfere with one another and cause the etalons, the etalons introducing the noise in absorption spectra of the light by the gases in the gas cell, and
wherein the three or more tunable diode lasers comprise a first tunable diode laser configured to emit first laser light in a wavelength range corresponding to a first contaminant in the gases and a second tunable diode laser configured to emit second laser light in a wavelength range corresponding to a second contaminant in the gases.

10. The system of claim 9, wherein the system further comprises a reflective collimation mirror positioned in an optical path between the combiner and the gas cell.

11. The system of claim 10, wherein the reflective collimation mirror has a parabolic reflection surface.

12. The system of claim 10, wherein the combiner includes an optic fiber configured to transmit the combined laser light toward the reflective collimation mirror, the optic fiber having an angled end facing the reflective collimation mirror.

13. The system of claim 9, wherein the three or more tunable diode lasers include a first tunable diode laser configured to emit first laser light in a first wavelength range in a vicinity of 1574.5 nm.

14. The system of claim 9, wherein the three or more tunable diode lasers include a first tunable diode laser configured to emit first laser light in a first wavelength range corresponding to an absorption range of $H_2S$ and $CO_2$.

15. The system of claim 9, wherein the three or more tunable diode lasers include a second tunable diode laser configured to emit second laser light in a second wavelength range in a vicinity of 1314 nm.

16. The system of claim 15, wherein the three or more tunable diode lasers include a second tunable diode laser configured to emit second laser light in a second wavelength range corresponding to an absorption range of $H_2O$.

17. The system of claim 9, wherein the one or more tunable diode lasers include a third tunable diode laser configured to emit third laser light in a third wavelength range in a vicinity of 760 nm.

18. The system of claim 9, wherein the three or more tunable diode lasers include a third tunable diode laser configured to emit third laser light in a third wavelength range corresponding to an absorption range of $O_2$.

19. The system of claim 9, wherein the system further comprises a plurality of pumps.

20. The system of claim 19, wherein the system comprises three pumps.

* * * * *